United States Patent [19]
Nüesch

[11] Patent Number: 6,045,529
[45] Date of Patent: Apr. 4, 2000

[54] DRIVE UNIT FOR A BREASTPUMP

[75] Inventor: Hansueli Nüesch, Remetschwil, Switzerland

[73] Assignee: Nüesch Logistik, Zuzwil, Switzerland

[21] Appl. No.: 09/165,063

[22] Filed: Oct. 2, 1998

[51] Int. Cl.[7] .................................................. B61M 1/06
[52] U.S. Cl. .............................. 604/74; 604/118; 604/346
[58] Field of Search ............................ 604/74, 118, 119, 604/346, 246, 247

[56] References Cited

U.S. PATENT DOCUMENTS

| | | |
|---|---|---|
| 3,238,937 | 3/1966 | Stein . |
| 4,964,851 | 10/1990 | Larsson . |
| 5,007,899 | 4/1991 | Larsson . |
| 5,810,772 | 9/1998 | Niederberger . |

*Primary Examiner*—John D. Yasko
*Attorney, Agent, or Firm*—Martin A. Farber

[57] ABSTRACT

A drive unit is disclosed for at least one breastpump for pumping mother milk by sucking it from a breast hood to be applied on a mother's breast by means of a breast pump connected to a breast hood through a pathway including a conduit and a vacuum chamber shut by a check valve against a milk collecting space, the drive unit comprising valve means for intermittently connecting and disconnecting the breast pump with a pathway, a valve means including actuating means for providing the intermittent connecting and disconnecting movement;

first drive means for the actuating means;

second drive means for driving the breast pump for providing a sucking effect; and speed varying means connected to and controlling at least one of the first and second drive means.

9 Claims, 2 Drawing Sheets

DRIVE UNIT FOR A BREASTPUMP

FIELD OF THE INVENTION

This invention relates to a drive unit for a breast pump. Breast pumps are usually used for pumping mother milk from a breast shield or hood to be applied on a mother's breast. Pumping is done by means of the pumping unit which is connected to the breast hood through a pathway which includes a conduit and a vacuum chamber. The vacuum chamber is shut at its lower end by a check valve against a milk collecting space so as to allow milk flowing towards the collecting space or vessel, often in the form of a detachable milk bottle, while preventing sucking milk from the collecting space.

BACKGROUND OF THE INVENTION

Breast pumps are used by mothers to collect milk in those occasions when natural breastfeeding is not possible. These include physical separation between the mother and the infant (i.e. hospitalized mother or infant), physiological difficulties related to the mother or the infant (i.e. oversensitive breasts, premature infant etc.), social separation between the mother and the infant (i.e. working mothers) etc.

A healthy child sucks usually at a frequency of about 15 to 60, generally 40 to 60, and in average 50 cycles per minute. Usually the infant sucks faster at the beginning to stimulate the breast until milk starts to flow and then sucks constantly at a more or less constant speed. The suction cycle of the infant consists of three parts, first with the building-up of vacuum through suction during which milk is extracted from the breast, then by breaking the vacuum by allowing air into the mouth through the mouth or the nose and finally by swallowing the milk and breath.

A breast pump, being complementary to the natural breastfeeding, should offer the mother the best possible simulation of the natural breastfeeding process. Some pumps simulate the suction cycle of the infant manually or semi-automatic, usually through manual breaking of the vacuum by the mother. The disadvantage of this, however, is that with these pumps each suction cycle takes several seconds to be completed and therefore leads to a cycle speed much lower than the cycle speed of a healthy infant. Other pumps use auto-cycle suction systems that simulate better the natural feeding process. Here too, even in the most sophisticated pumps conceivable which include a speed regulation, the suction strength is not constant, but depends on the suction speed.

Another approach is has been suggested in the copending PCT Application No. WO 98/26817. There is a flow regulator which supplies by-passing additional air into the suction pathway. However, it has been found out that with such an arrangement it is not possible to maintain constant conditions with respect to air flow's intensity, if one would attempt to vary the speed of the driving motor in order to modify the suction frequency.

SUMMARY OF THE INVENTION

Therefore, it is an object of the present invention to provide a drive unit for a breast pump of the kind described which is easily adaptable to special requirements by changing its characteristics.

Another object of the present invention is to maintain a desired suction strength or intensity constant even if varying the suction frequency.

These objects are achieved by providing separate driving arrangements for driving the valve (that determines the suction frequency), on the one hand, and for driving the pump, on the other hand, the latter determining the suction intensity. Moreover, a speed varying device is provided and is connected to and controls at least one of the driving arrangements. In this way, it is possible to vary the suction frequency without affecting the intensity or vice-versa.

In principle, it would be possible to have a single driving motor and least one speed varying gear for driving at least one of the pump or the valve. More favorable is it, however, if both driving arrangements comprise each an electric motor.

Depending on the application of a breast pump either in hospital or at home, different kinds of motors could be used. It is preferred, however, to use a DC-motor at least as one of the motors. For example, a common pumping drive for a plurality of connections in a hospital to connect one or more breast pumps [containing a valve drive, breast hood(s) etc.] could comprise an AC-motor, the speed of which could e.g. be varied in accordance to the number of breast pumps connected by a frequency converter, if desired could be used, while each individual valve is driven by a DC-motor. In such a case, it would be conceivable to provide a sensor switch at each connection so that the speed of the AC-motor could be varied automatically. An alternative could reside in that an air pressure sensor maintains suction pressure constant by varying the speed of the AC-motor accordingly. However, in most cases it will be desirable to use DC-motors for both driving arrangements.

Certainly, it would be likewise possible to vary the speed of the pumping drive or to vary the valve drive or both. It is, however, preferred that the speed varying device controls at least the latter. Tests have shown that if the pumping speed is maintained constant, the intensity remains, generally, constant even with varying suction frequency. The reason is that with increasing frequency the opening periods of the valve (as well as the closing periods) become generally shorter so that the same amount of air flow or pressure is used per time unit. This, however, depends on the type of valve and its actuation: If the opening and closing periods are interrelated (e.g. with magnetically actuated valves, i.e. if an electromagnet forms the respective driving arrangement), it could be conceivable to vary also the relationship between the opening and closing periods, e.g. by an electronic device. In such a case, it could be useful to vary the speed of both arrangements, e.g. in accordance with a certain characteristic specific to this relationship. In this respect, the term "speed varying means", as used herein, should also encompass a device which varies this relationship.

It has been already mentioned that for varying the speed a variable gear drive could be used. If, however, an electromagnetic drive (in the broadest sense of this term encompassing also a motor) is used, it is preferable to provide an electric varying device. Such an electric device could comprise a frequency converter (as mentioned above) or a clock generator feeding an RC-circuit, the clock frequency being variable. Such variation could be provided by having a clock generator of a fixed, relative high frequency and to provide frequency dividers at its output to be switched and/or combined into an operative state by an appropriate switching stage. In a preferred embodiment according to the invention the speed varying device comprises a potentiometer or a pulse width modulation circuit. In the latter case, such a circuit could vary the relationship between closure periods and opening periods of the valve mechanism by feeding pulses of a desired width and a desired interval between the pulses either to the valve actuating magnet(s) or a stepping motor which drives intermittently the corresponding valve in accordance with the pulses supplied.

BRIEF AND DETAILED DESCRIPTION OF THE DRAWING

Further details will become apparent from the following description of preferred embodiments of the invention shown in the drawings in which FIG. 1 shows a perspective view of a drive unit according to the present invention for providing suction to two breast pumps to be applied on both breasts of a mother; and FIG. 2 depicts another perspective view of an especially preferred embodiment.

DETAILED DESCRIPTION OF THE DRAWINGS

Figure 1:
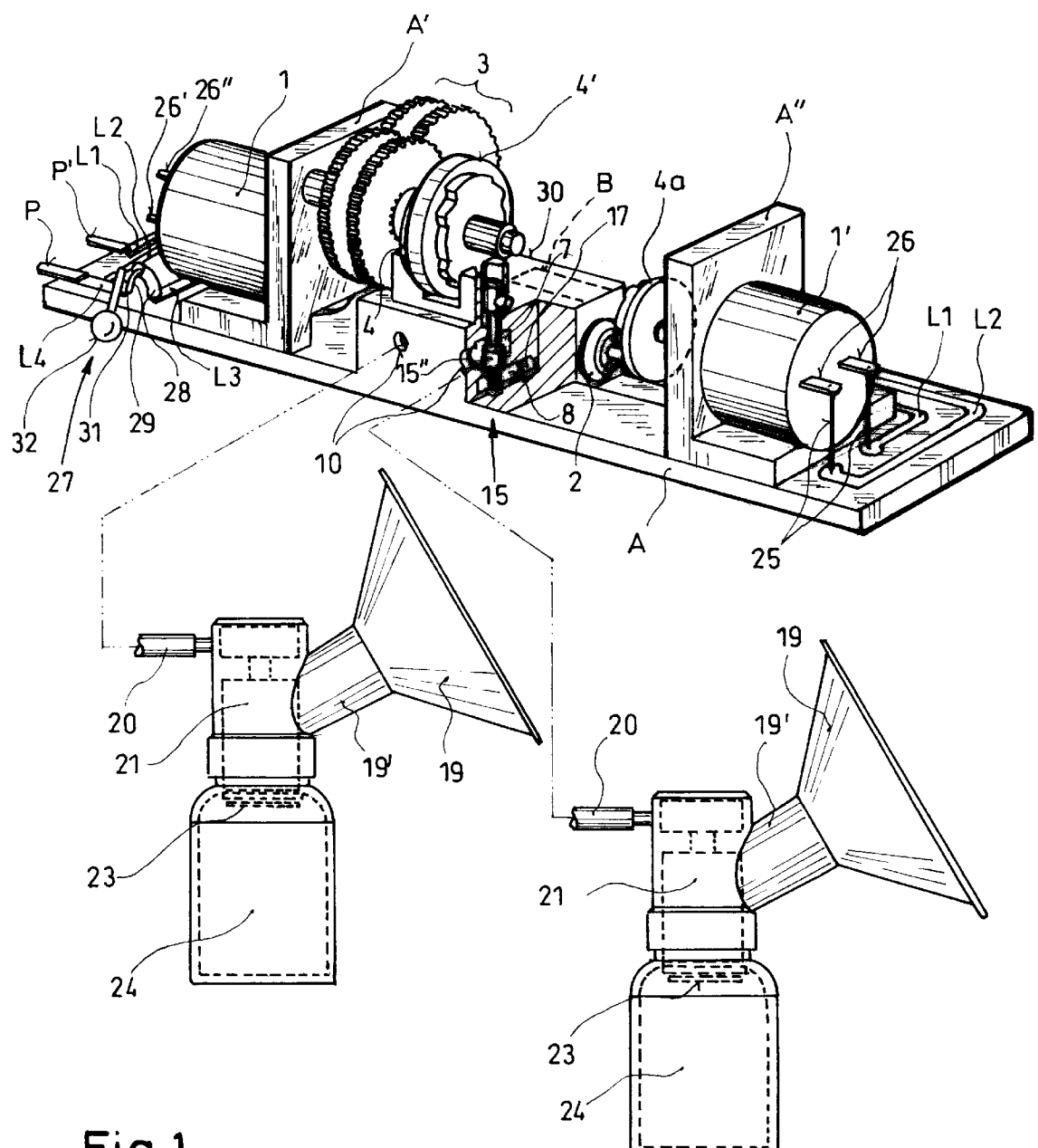

On a component carrier A (FIG. 1), first and second bearing walls A' and A" are fixed by rivets, screws or an adhesive. Each bearing walls supports an electric DC, battery driven motor 1 and 1', the battery being not shown, but has to be connected through connecting plugs P, P' mounted on carrier A. As is indicated by printed electrically conductive lines L, the carrier A forms, preferably, a printed circuit board or carries such a board on one of its surfaces. This carrier A together with its components, to be described below, are shown at an enlarged scale in comparison with two breast pumps shown beneath the drive unit represented above them in the figure. In general, such a drive unit will be incorporated at the top of at least one of the breastpumps shown at a reduced scale in the drawing to form an independently operable unit, but the invention is not limited to that.

The DC-motor 1 drives a reducing gear 3 for providing drive to radial cams 4, 4' (the controlling cam surface being the peripheral surface) at a reduced rate of revolutions per minute. The DC-motor 1' drives a membrane or diaphragm pump 2, or any other type of pump, via an axial cam 4a (where the controlling cam surface is the surface facing the pump 2). This pump 2 is arranged on a wall defining a vacuum space B inside a block 30 which forms a common housing both for the vacuum space B and a valve mechanism generally referenced 15. Thus, the motor 1, the gear 3 and the cams 4, 4' form a driving and actuating (the cams) arrangement for the valve 15. This valve 15, as represented, is preferably designed in the manner described in WO 98/30257, but may, optionally, also be formed as disclosed in EP-A-0 744 180 the whole contents of both of which being incorporated here by reference. However, the invention is not limited to the use of a specific valve unit 15.

In this way, suction pressure accumulated in the space B is distributed over outlet openings 17 (only one is shown), enters a transverse channel 8 and is either released by opening a valve body 15" in a valve chamber 7 or is confined by it within the channel 8. The arrangement on the side of the cam 4 is practically the same with the exception that there the valve body closes its chamber 7 against the channel 8, while the valve body 15" assigned to the actuating cam 4' provides a communication between the respective chamber 7 and channel 8, and vice-versa. Since each one of the valve chambers 7 has an outlet 10, this outlet 10 is subjected to substantially the same subpressure or suction as its chamber 7.

Both outlets 10 are connected to hoses 20 mainly shown in dash-dotted lines to apply suction to each one of two breast pump units each comprising a breast hood 19 through a conduit 19' and a vacuum chamber 21 which is shut at its lower end by a check valve 23 against a milk collecting space 24 below. In this way, a single drive unit on the carrier A may provide suction to two breast pumps to be applied to both breasts of a mother simultaneously.

The circuit on the carrier A for energizing the two motors 1, 1' starts from the plugs P, P'. A starter switch is not shown, but is interconnected into the two lines L1, L2, immediately after the plugs P, P'. While lines L1, L2 run around the carrier A to energize motor 1' directly via wires 25 and lugs 26. In contrast, a lug 26' of motor 1 is connected to line L1 directly, while lug 26" of motor 1 is connected to line L3 in a manner not shown. Line L3 is the output line of a potentiometer, generally referenced 27, comprising a resistor 28 which is tapped by a slicing contact 29 fixed on a short shaft 31. Shaft 31 is in electrically conductive connection with a line L4 which is in direct connection with plug P, on the one hand, and from which line L2 branches off.

In this way, motor 1 is energized via the potentiometer and is supplied with a voltage the magnitude of which depends on the setting of the potentiometer 27. To be able to adjust the setting of the potentiometer 27, shaft 29 is provided with a handle 32 suitably protruding to outside. Optionally, an electronic motor control stage is interposed, the purpose of which is described below.

A long carrier A, as in FIG. 1, might be subject to bending and/or vibrations which is especially inconvenient if it is formed by a printed circuit board where the conductors L1 to L4 are sensible to stress. Therefore, an arrangement according to FIG. 2 is preferred in which parts already described with reference to FIG. 1 have the same reference numerals.

Figure 2:
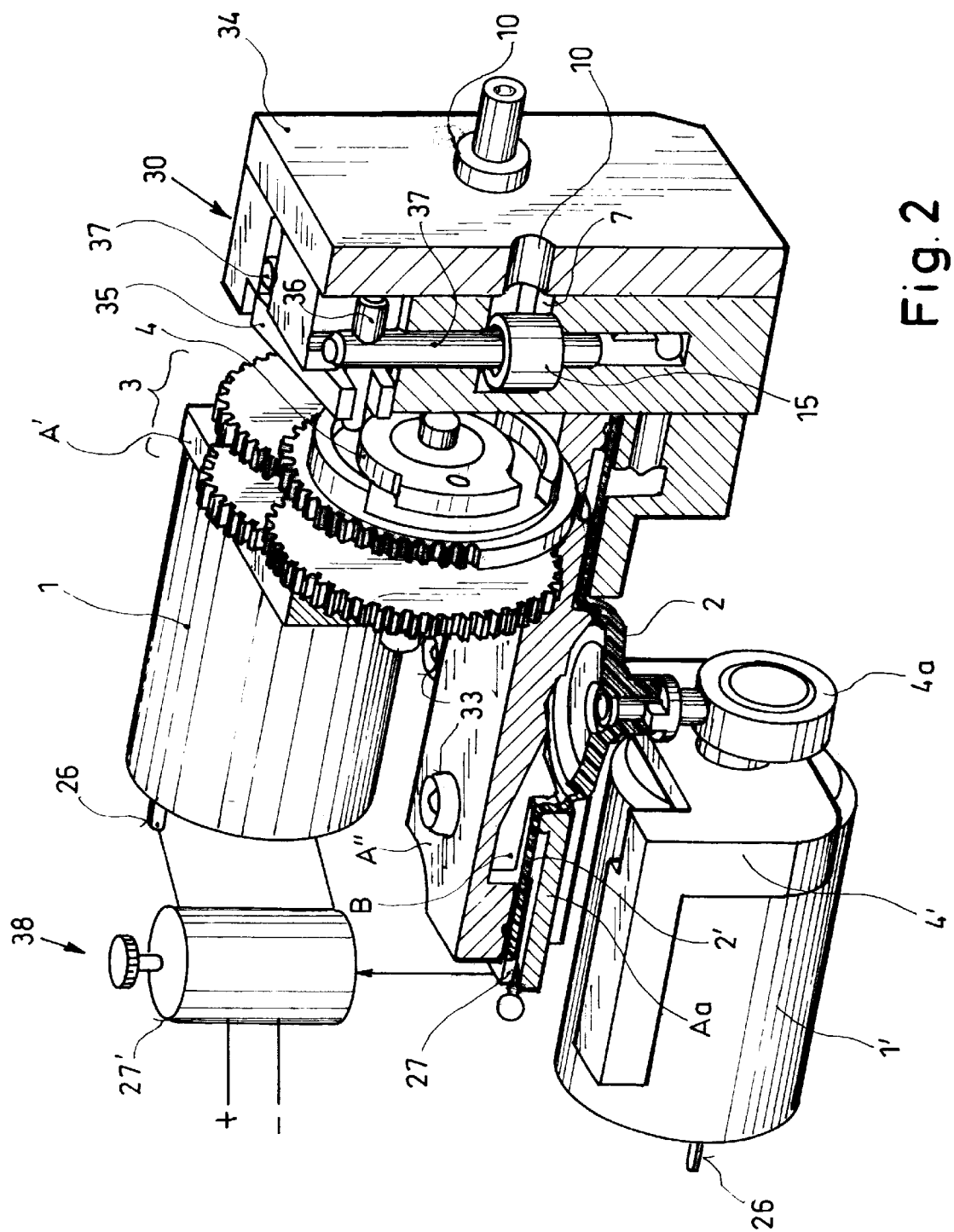

As may be seen from FIG. 2, the carrier A" is a composite carrier formed by a plurality of parts. While the upper part of carrier A" forms the hollow space B which is partly closed by the diaphragm 2' of pump 2. The diaphragm 2' is clamped to the upper part of the carrier A" by two lower parts Aa and Ab screwed or riveted to the upper part by pins (screws or rivets) 33 (only one is shown). Although a diaphragm pump is preferred, the present invention is not restricted to this type, but can use any type of pump conceivable. The block 30 may be formed integrally with the lower part Ab or separately. A closure plate 34 is fastened to the block 30 to close the chambers 7 and to form the outlets 10. A yoke Y for supporting a respective motor, such as motor 1', may either be integral with the lower part Aa of the carrier A" or may form a separate part fastened to the upper or lower part carrier A". Alternatively, a shield A' may be used as is shown in connection with motor 1.

In FIG. 2, the fork-like ends of a two-armed rocker lever 35 (as in WO 98/30257) embrace transverse studs 36 (only one is shown) passing each through a guide rod 37 of the respective valve body 15". The end of the stud 36 at right of FIG. 2 serves as a further guidance, whereas the left end engages a groove of cam 4. Since the two motors 1, 1' are mounted on opposite sides of the carrier A", the latter is shorter and more sturdy. Therefore, conductors and electronic parts, such as the potentiometer 27, are less liable to stress.

As is shown on the left side of FIG. 2, the potentiometer 27 is coupled to a motor control stage 27' preceding at least one of the motors 1, 1', particularly motor 1, which is fed via taps referenced "+" and "−". This control stage 27' may be provided with an adjusting device 38 for varying the relationship between closure periods and opening periods of the valve mechanism by feeding pulses of a desired width and a desired interval between the pulses. It is clear that the adjusting device may be of any type known in the art. When an adjusting device 38 is used, the motors 1, 1' may be formed by stepping motors so that one pulse (or a predetermined number of them) is used to turn the respective motor from the closing position of the valve body 15 to an open position, while the interval between two pulses determine the duration of the respective period. The same could be achieved if the valve bodies 15 are actuated by electromagnets rather than by motors.

While the invention has been described with reference to a preferred embodiment, it is by no means restricted to it, but numerous modifications are within the scope of the invention. For example, though the present example shows a single energizing circuit for both drive motors 1 and 1', they could be energized separately. Moreover, as mentioned above, a speed (or frequency) varying potentiometer or other device could likewise be assigned to drive 1'. Instead of the potentiometer 27, an electronic circuit could be used which, for example, has one output for each of the drives 1 and 1', the two outputs being interrelated according to a desired characteristic; this would especially apply, if at least one of the drives 1, 1' is formed by an electromagnet (in which case no cam 4, 4' or 4a would be necessary) to provide a reciprocating movement of either the pump 2 or the valve bodies 15" or both, and the relationship between closure periods and opening periods are made variable. The same effect can be achieved by using at least one stepping motor 1 (and 1'). In this case, the potentiometer 27 would be connected to a motor control stage which provides the necessary pulses to drive the motor 1 or 1'. However, using a pulse supplying stage makes it possible to form this stage in a manner as to vary the pulse width so that the relationship between closure periods and opening periods of the valve can be made variable.

Furthermore, the invention is not restricted to the use of two breast pump units including breast hoods or shields 19. In the case of a single breast pump, one of the cams 4 or 4' could be omitted. Instead of a printed circuit board, the carrier could carry a hybrid circuit or an IC. While only one gear 3 is shown, another reducing gear could be used in connection with motor 1', although it will, in general, not be necessary.

Instead of a single carrier A for both drives 1, 1', two separate carriers could be used. Although a collecting vessel or receptacle is shown, any other collecting facility could be provided, such as a hose leading to a remote collecting space.

An especially useful modification could consist in combining the present invention with an overflow protection, preferably as disclosed in German Patent Application No. 197 47 842.5 filed Oct. 30, 1997, the whole contents of which being incorporated here by way of reference. Whenever milk flows in such an amount that there is a risk that the pump becomes overflowed, a sensor can determine this condition and automatically reduce the pumping intensity. To this end, the overflow protection valve, particularly that of the German Patent Application mentioned above, when actuated by overflowing milk could switch a sensor switch either itself or over the membrane to which the valve of said German Patent Application is attached. The pump drive 1' could be connected to an electronic speed variator which, upon receiving the switch's input signal upon actuation, reduces the pumping intensity so that another milk overflow is not likely to occur, if desired, a timing stage may accelerate the drive 1' up to a desired "normal speed", if, for a given time, no flooding occurs. It has to be understood that the sensor could be of any type, e.g. being formed by a level sensor for sensing the milk level, or the maximum milk level only, within the suction or vacuum chamber 21. It is also clear that such a control necessitates an automatic setting device rather than a manual one, as shown by handle 32.

An alternative to the above speed variation for overflow protection could reside in changing the relationship between the opening periods and the closing periods of the valve 15. This means, in general, that a further aspect of the present invention consists in a sensor arrangement for sensing the milk flooding risk, and controlling a device for changing at least one parameter which affects the air flow intensity. In this sense, it would also be conceivable to vary the effective opening of a by-passing air stream in an air flow regulator as disclosed in the above mentioned WO 98/26817.

What is claimed is:

1. A drive unit for at least one breastpump for pumping mother milk by sucking it from a breast hood to be applied on a mother's breast by means of said breast pump connected to said breast hood through a pathway including a conduit and a vacuum chamber shut by a check valve against a milk collecting space, the drive unit comprising valve means for intermittently connecting and disconnecting said breast pump with said pathway, said valve means including actuating means for providing the intermittent connecting and disconnecting movement;

first drive means for said actuating means;

second drive means for driving said breast pump for providing a sucking effect; and speed varying means connected to and controlling at least one of said first and second drive means.

2. Drive unit as claimed in claim 1, wherein each of said first and second drive means comprise an electric motor.

3. Drive unit as claimed in claim 2, wherein at least one of said motors is a DC-motor.

4. Drive unit as claimed in claim 1, wherein said speed varying means control at least said first drive means.

5. Drive unit as claimed in claim 1, wherein said speed varying means comprise a potentiometer.

6. A drive unit for at least one breastpump for pumping mother milk by sucking it from a breast hood to be applied on a mother's breast by means of said breast pump connected to said breast hood through a pathway including a conduit and a vacuum chamber shut by a check valve against a milk collecting space, the drive unit comprising valve means for intermittently connecting said breast pump with said path way during an opening period, and for disconnecting said breast pump from said path way during a closure period, said valve means including actuating means for providing intermittent connecting and disconnecting movement;

first drive means for said actuating means;

second drive means for driving said breast pump for providing a sucking effect; and speed varying means connected to and controlling at least one of said first and second drive means;

common carrier means for mounting said first and second drive means, said valve means and said speed varying means.

7. Drive unit as claimed in claim 6, wherein said speed varying means comprise a potentiometer.

8. Drive unit as claimed in claim 6, further comprising means for varying the relationship between said closure and opening periods of said valve means.

9. Drive unit as claimed in claim 6, wherein said common carrier means comprise a printed circuit board.

* * * * *